United States Patent [19]

Umio et al.

[11] 3,992,409

[45] Nov. 16, 1976

[54] 1-ALKANESULFONYLOXYALKYL-2-ALKYL-3-DIPHENYLMETHYLENEPYR-ROLIDINES

[75] Inventors: Suminori Umio, Kawanishi; Shizuo Maeno, Osaka, both of Japan

[73] Assignee: Fujisawa Pharmaceutical Co., Ltd., Osaka, Japan

[22] Filed: June 18, 1975

[21] Appl. No.: 587,855

[52] U.S. Cl. .......................... 260/326.82; 424/274
[51] Int. Cl.$^2$ .................................. C07D 207/20
[58] Field of Search ........................... 260/326.82

[56] References Cited
UNITED STATES PATENTS 3,699,125  10/1972  Umio et al. .................. 260/326.81

OTHER PUBLICATIONS

Wagner et al. *Synthetic Organic Chemistry*, (1953) p. 823.

*Primary Examiner*—Nicholas S. Rizzo
*Assistant Examiner*—Mary C. Vaughn
*Attorney, Agent, or Firm*—Dayton R. Stemple, Jr.

[57] ABSTRACT

This invention relates to novel 1-alkanesulfonyloxyalkyl-2-alkyl-3-diphenylmethylenepyrrolidines, their acid addition salts and preparation thereof, having anticolinergic activity.

3 Claims, No Drawings

1-ALKANESULFONYLOXYALKYL-2-ALKYL-3-DIPHENYLMETHYLENEPYRROLIDINES

The 1-alkanesulfonyloxyalkyl-2-alkyl-3-diphenylmethylenepyrrolidines of this invention may be represented by the following formula:

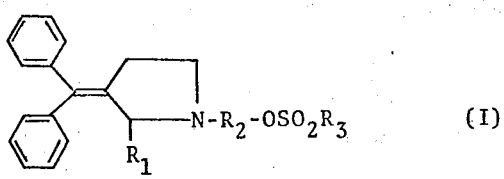

(I)

wherein $R_1$ and $R_3$ are each alkyl and $R_2$ is alkylene.

Herein-before and -after, the term "alkyl" for the symbols $R_1$ and $R_3$ is a monovalent radical of a straight or branched hydrocarbon, preferably having 1 to 6 carbon atom(s), for example, methyl, ethyl, propyl, isopropyl, butyl, isobutyl, tert-butyl, pentyl and hexyl; and the term "alkylene" for the symbol $R_2$ is a bivalent radical of a straight or branched hydrocarbon, preferably having 1 to 6 carbon atom(s), for example, methylene, ethylene, propylene, trimethylene, tetramethylene, pentamethylene, hexamethylene and 2-methyltrimethylene.

The compounds (I) and the acid addition salts threof have anticolinergic activity and are valuable as a gastric secretion inhibitory or anticonvulsant agent.

Accordingly, a basic object of this invention is to provide the compounds (I) and the acid addition salts thereof. Another object of this inventon is to provide a process for preparation of the compounds (I) and the acid addition salts thereof.

These and other objects will be apparent to the conversant with the art to which this invention pertains from the subsequent descriptions.

According to this invention, the compounds (I) and the acid addition salts thereof may be prepared by reacting a 2-alkyl-3-diphenyl-methylenepyrrolidine compound of the formula:

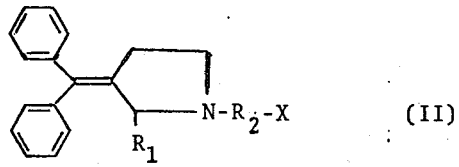

(II)

wherein $R_1$ and $R_2$ are each as defined above, and X is hydroxy or halogen (e.g. chlorine, bromine or iodine), or its acid addition salt with an alkanesulfonic acid of the formula:

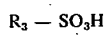  III wherein $R_3$ is as defined above, or its reactive derivative.

In the precess of this invention, the acid addition salts of the compounds (I) and (II) may be inorganic acid addition salts such as hydrohalide (e.g. hydrochloride or hydrobromide), sulfate or nitrate, and organic acid addition salts such as trifluoroacetate, malonate, maleate, fumarate, tartrate, citrate, methanesulfonate or p-tolueneacetate; and the reactive derivatives of the compounds (III) may be mixed anhydrides with dialkylphosphoric acids, diphenylphosphoric acid, dibenzylphosphoric acid, halogenated phosphoric acids, dialkylphosphorous acids, thiosulfuric acid, hydrohalogenic acids (e.g. hydrochloric acid) or sulfuric acid; symmetric acid anhydrides, and salts with metals selected from the group of the group I metal (e.g. lithium, sodium, potassium, copper or silver), the group II metal (e.g. magnesium, calcium or mercury) and the group VIII (e.g. cobalt) of Periodical Table. Among them, the mixed anhydrides of the compounds (III) with hydrohalogenic acids are preferably used in case of the reaction with the compounds (II) wherein X is hydroxy, and the salts of the compounds (III) with metals such as silver are preferably used in case of the reaction with the compounds (II) wherein X is halogen.

The reaction of the process of this invention is usually carried out in a solvent which gives no unfavorable influence on the reaction. The reaction may be conducted, when desired, in the presence of an inorganic base such as an alkali metal hydroxide (e.g. sodium hydroxide or potassium hydroxide), an alkaline earth metal hydroxide (e.g. calcium hydroxide or magnesium hydroxide), an alkali metal carbonate (e.g. sodium carbonate or potassium carbonate) or an alkaline earth metal carbonate (e.g. calcium carbonate or magnesium carbonate), or an organic base such as trimethylamine, triethylamine, N,N-dimethylaniline, N,N-dimethylbenzylamine, N-methylpiperazine, pyridine, quinoline, or a tertiary ammonium base (e.g. benzyltriethylammonium hydroxide or tetramethylammonium hydroxide). These bases can be used solely or in a mixture thereof and, when they are in liquid, may be employed as a solvent.

The reaction of the free alkane sulfonic acids (III) with the compounds (II) wherein X is hydroxy can be carried out advantageously in the presence of a condensing agent such as N,N-dicyclohexylcarbodiimide, N-cyclohexyl-N'-morpholinoethylcarbodiimide, N-cyclohexyl-N'-(4-diethylaminocyclohexyl) carbodiimide, N,N'-diethylcarbodiimide, N,N'-diisopropylcarbodiimide, N-ethyl-N'-(3-dimethylaminopropyl)carbodiimide, N,N'-carbonyldi(2-methylimidazole), pentamethyleneketene-N-cyclohexylimine, diphenylketene-N-cyclohexylimine, alkoxyacetylene, 1-alkoxy-1-chloroethylene, trialkyl phosphite, ethyl polyphosphate, isopropyl polyphosphate, phosphorous oxychloride, phosphorous trichloride or thionyl chloride.

The reaction temperature can vary widely and the reaction is carried out usually under cooling or at ambient temperature.

The reaction product can be isolated and purified according to conventional methods.

Thus obtained compounds (I) are converted to desired acid addition salts thereof by treating the compounds (I) with the corresponding acids according to conventional manners. Thus obtained salts of compounds (I) are more stable and therefore can be conveniently employed in the manufacturing and the therapeutical use.

The compounds (I) and their acid addition salts of this invention are possessed of anticholinergic activity and are of value as medicines such as a gastric secretion inhibitory or anticonvulsant agent.

In practical administration for therapeutical purpose, the acid addition salts of the compounds (I) are to be used in a form of the non-toxic pharmaceutically acceptable salts.

The compounds (I) and their non-toxic pharmaceutically acceptable salts can be administered by the conventional methods, the conventional types of unit dosages, or with the conventional pharmaceutical carriers to produce a designated therapeutic effect.

Thus, they can be used in the form of pharmaceutical preparations, which contain them in admixture with a pharmaceutical organic or inorganic carrier material suitable for enteral or parenteral applications. Oral administration by the use of tablets, capsules or in liquid form such as suspensions, solutions or emulsions, is particularly advantageous.

The invention is illustrated by the following examples.

EXAMPLE

A solution of 1-(2-hydroxyethyl)-2-methyl-3-diphenylmethylenepyrrolidine (880 mg) in dry acetone (40 ml) was cooled with ice-water, and mesylchloride (350 mg) in dry acetone (3 ml) was added dropwise thereto under stirring. The resultant mixture was kept stirred for 3 hours. Precipitates were filtered off and the filtrates were evaporated to dryness under reduced pressure. The residue was dissolved in water (20 ml) and ether (15 ml) was added thereto, which was neutralized by adding dropwise 5% aqueous sodium bicarbonate solution under cooling. The ether layer was separated out and the aqueous layer was washed with ether (15 ml). The washings and the ether layer were combined together, washed twice with cold water and dried over magnesium sulfate. The magnesium sulfate was filtered off and anhydrous ethanolic solution (0.4 g) containing dry hydrogen chloride (100 mg) was added dropwise to the filtrates with shaking occasionally. The mixture was allowed to stand at room temperature. The precipitates were collected by filtration and washed with anhydrous ether and then dried to give colorless fine needles (250 mg) of 1-(2-mesyloxyethyl)-2-methyl-3-diphenylmethylenepyrrolidine hydrochloride, m.p. 150° to 151° C.

The ether solution of 1-(2-mesyloxyethyl)-2-methyl-3-diphenylmethylenepyrrolidine obtained in a similar manner to that of the above example was treated with methanesulfonic acid, maleic acid, malonic acid and fumalic acid, respectively to give the corresponding salts mentioned below:

|   | Salt of (I) | mp (° C) |
|---|---|---|
| 1) | Methanesulfonate | 120 to 123 |
| 2) | Maleate | 101 to 103 |
| 3) | Malonate | 88 to 90 |
| 4) | Fumarate | 106 to 108 |

What we claim is:
1. A compound of the formula

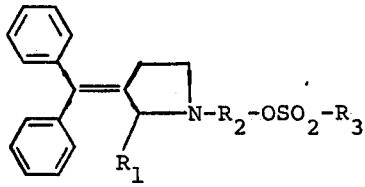

wherein $R_1$ and $R_3$ are each alkyl of 1–6 carbons and $R_2$ is alkylene of 1–6 carbons, and a non-toxic, pharmaceutically acceptable acid addition salt thereof.

2. A compound according to claim 1, wherein $R_1$ and $R_3$ are methyl and $R_2$ is ethylene.

3. A compound according to claim 2, wherein the salt is a hydrochloride, methanesulfonate, maleate, malonate or fumarate.

* * * * *